United States Patent
Neumeyer

(10) Patent No.: US 8,894,411 B2
(45) Date of Patent: Nov. 25, 2014

(54) SYSTEM FOR PREPARING AND DISPLACING TISSUE

(75) Inventor: Stefan Neumeyer, Eschlkam (DE)

(73) Assignee: Gebr. Brasseler GmbH & Co. KG, Lerngo (DE)

(*) Notice: Subject to any disclaimer, the term of this patent is extended or adjusted under 35 U.S.C. 154(b) by 0 days.

(21) Appl. No.: 13/254,067

(22) PCT Filed: Mar. 5, 2010

(86) PCT No.: PCT/DE2010/000241
§ 371 (c)(1),
(2), (4) Date: Sep. 22, 2011

(87) PCT Pub. No.: WO2010/099791
PCT Pub. Date: Sep. 10, 2010

(65) Prior Publication Data
US 2012/0015324 A1    Jan. 19, 2012

(30) Foreign Application Priority Data
Mar. 6, 2009  (DE) .................. 10 2009 011 584

(51) Int. Cl.
*A61C 3/02* (2006.01)
*A61C 1/14* (2006.01)

(52) U.S. Cl.
CPC ..................... *A61C 1/148* (2013.01)
USPC .......................... 433/118; 433/125

(58) Field of Classification Search
USPC ................... 433/118, 122, 124, 125
See application file for complete search history.

(56) References Cited

U.S. PATENT DOCUMENTS 2,100,319 A * 11/1937 Brown et al. ............... 433/122
3,073,031 A * 1/1963 Brenman et al. ............ 433/122
3,292,674 A * 12/1966 Turner ........................ 83/848
4,432,729 A * 2/1984 Fattaleh ...................... 433/118
4,544,356 A * 10/1985 Gardella et al. ............. 433/122
4,813,324 A * 3/1989 Yoshida et al. .............. 83/848
4,954,082 A * 9/1990 Weissman .................... 433/80
5,402,580 A * 4/1995 Seto et al. ..................... 30/394
5,505,617 A * 4/1996 Skeppmark et al. ........ 433/118
5,569,257 A * 10/1996 Arnegger et al. ............ 606/82
6,062,858 A * 5/2000 Hugo et al. .................. 433/119
6,106,290 A * 8/2000 Weissman .................... 433/122
6,220,139 B1 * 4/2001 Kobayashi et al. .......... 83/835
6,267,594 B1 * 7/2001 Hugo ........................... 433/119
6,269,722 B1 * 8/2001 Hellbergh .................... 83/661
6,860,886 B1 * 3/2005 Lee .............................. 606/82
7,785,106 B2 * 8/2010 Takahashi ................... 433/166
2001/0004695 A1    6/2001 Vercellotti et al.

FOREIGN PATENT DOCUMENTS

| CH | 615339 | 1/1980 |
| DE | 545369 | 3/1932 |
| DE | 19825261 | 12/1999 |
| DE | 10 2004 002868 | 3/2005 |
| DE | 102004002868 | 3/2005 |
| EP | 1224913 | 7/2002 |

* cited by examiner

*Primary Examiner* — Ralph Lewis
(74) *Attorney, Agent, or Firm* — Welsh Flaxman & Gitler LLC

(57) ABSTRACT

A dental handpiece to which various tools forming a tool set can be coupled, and more precisely a handpiece coupling, which can be driven by a drive in the dental handpiece at least for an axial oscillating motion The coupling is constituted for a connection of the tools by insertion and securing, and more precisely with a conically tapering opening, into which an adapted coupling section of the tools that tapers in the shape of a truncated cone can be introduced and secured in a suitable manner.

9 Claims, 9 Drawing Sheets

SYSTEM FOR PREPARING AND DISPLACING TISSUE

BACKGROUND OF THE INVENTION

The invention relates to a system for preparing and displacing tissue.

A problem addressed by the invention is to provide a system with which the preparation and careful displacement of tissue is also possible in the area of dental medicine and/or dental surgery.

A system including a handpiece with a drive, and a handpiece coupling which can be driven in an oscillating manner is provided to solve this problem.

Developments, advantages and possible applications of the invention also emerge from the following description of examples of embodiment and from the figures. All the features described and/or graphically represented are fundamentally the subject-matter of the invention in themselves or in an arbitrary combination, irrespective of their combination in the claims and their back-references.

BRIEF DESCRIPTION OF THE DRAWINGS

The invention is explained in greater detail below with the aid of FIGS. 1-18, which show various instruments of the oscillating system for preparing and displacing tissue according to the invention.

DESCRIPTION OF THE PREFERRED EMBODIMENTS

Figure 1:
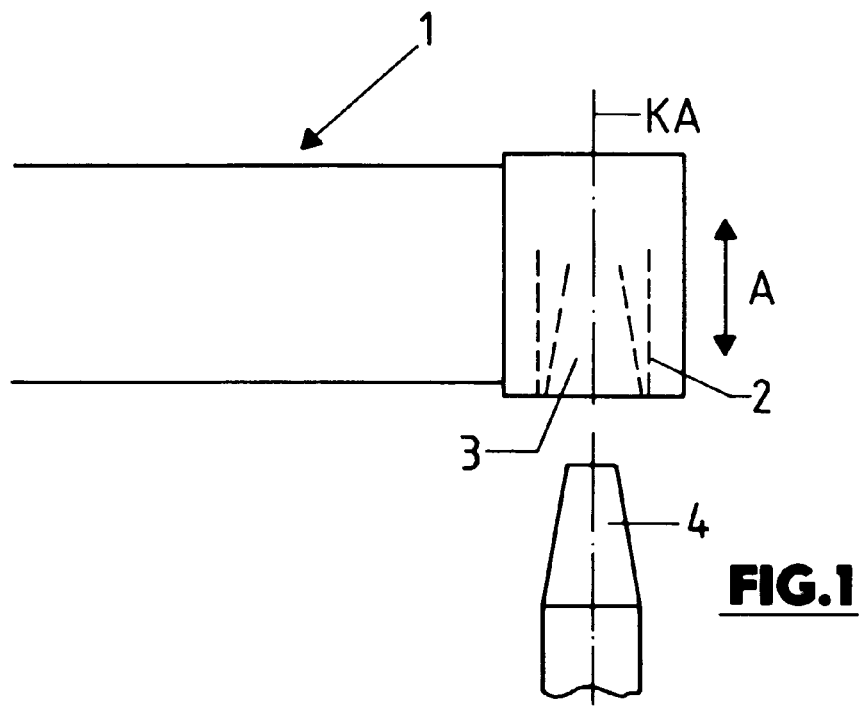
FIG. 1 is a side view of a dental handpiece, coupling and breakaway section of a dental tool.
Figure 2:
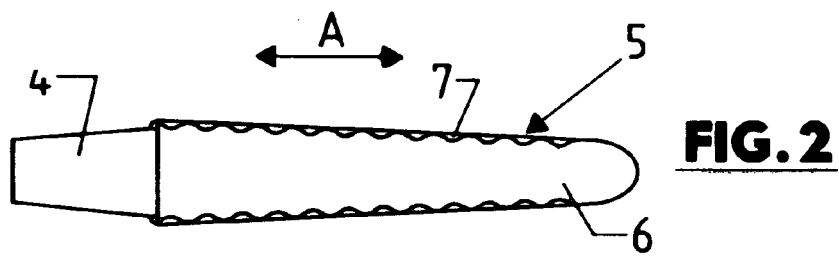
FIG. 2 is a side view of a dental tool for use with the dental handpiece and coupling.

In FIG. 1, dental handpiece 1 is shown to which various tools forming a tool set can be coupled, and more precisely a handpiece coupling 2, which can be driven by a drive in handpiece 1 at least for an axial oscillating motion, i.e. corresponding to the double arrow of FIG. 1 for an oscillating motion in axis KA of a coupling 2. The coupling 2 is constituted for a connection of the tools by insertion and securing, and more precisely with a conically tapering opening 3, into which an adapted coupling section 4 of the tools that tapers in the shape of a truncated cone can be introduced and secured in a suitable manner, for example by latching, by means of a thread and/or by a bayonet-type locking arrangement.

The stroke of the oscillating motion generated by handpiece 1 lies in the range between 0.05 and 1 mm. Handpiece 1 is preferably constituted such that both the frequency of the oscillating motion as well as the stroke of this motion can be adjusted independently of one another.

The system comprises a tool set with different tools, for example with the tools represented in FIGS. 2-10. Tool 5 represented in FIG. 2 essentially comprises a flat, elongated tool body 6, which is provided at one end with coupling section 4 and is constituted saw-like at its edge regions with a plurality of recesses 7. At the surface sides, flat tool body 6 is provided with a roughened surface in the manner of a file, by suitable surface structuring and/or by particles applied to the surface sides forming a rough outer face.

Figure 3:
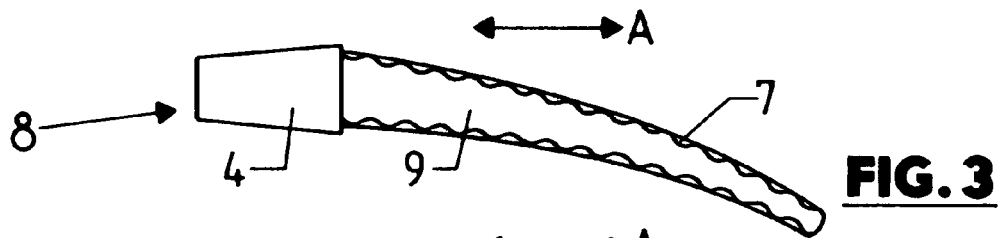
FIG. 3 is a side view of an alternate embodiment of a dental tool for use with the dental handpiece and coupling.

FIG. 3 shows a tool 8, which differs from the tool 5 essentially in that the tool body 9 has a curved shape, i.e. curved at the longitudinal edges, but is otherwise again constituted in a plane.

Figure 4:
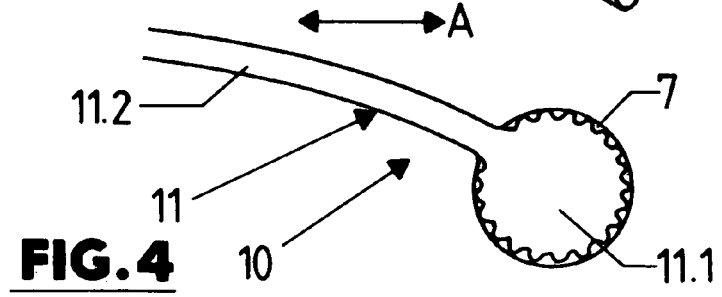
FIG. 4 is a side view of an alternate embodiment of a dental tool with the section that attaches to the coupling not shown.

FIG. 4 shows a tool 10, and a tool body 11 which is constituted widened in the manner of a spoon at the end lying away from coupling section 4, wherein recesses 7 forming the saw-like structure are provided in this embodiment only on widened section 11.1 of the tool body. Section 11.1 of tool body 11 extending from section 11.1 to coupling section 4 is constituted curved.

Figure 5:
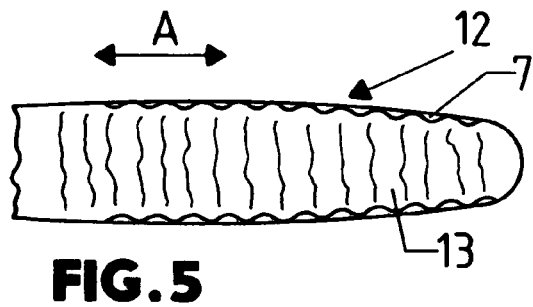
FIG. 5 is an alternate embodiment of a side view with the section that attaches to the coupling not shown.
Figure 6:
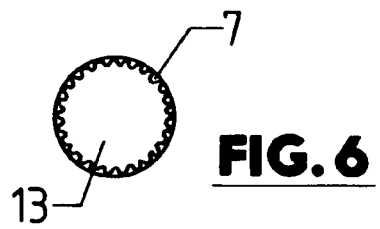
FIG. 6 is a cross-section of the dental tool shown in FIG. 5.

FIGS. 5 and 6 show in side view and in cross-section a tool 12, tool body 13 whereof, differing from tool bodies 6, 9 and 11, is not constituted flat, but rather "three-dimensionally" with a round or roughly round cross-section. At the outer face, tool body 13 is again provided saw-like with a plurality of recesses 7. Tool body 13 of tool 12 can also has a cross-section diverging from the circular shape, for example an oval or polygonal cross-section.

Figure 7:
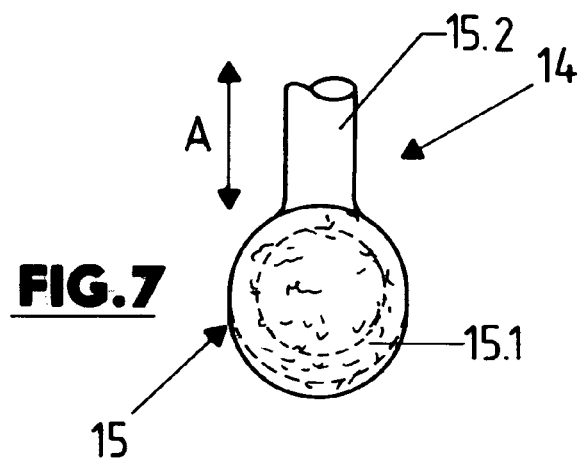
FIG. 7 is an alternate embodiment of a side view of a dental tool with the section that attaches to the coupling not shown.

A likewise "three-dimensional" tool 14 is represented in FIG. 7. The tool body 15 is constituted in this embodiment, at its end lying away from coupling section 4, with a section 15.1 in the shape of a round, enlarged head piece. Section 15.1 is connected to a ram-like section 15.2 with a reduced cross-section, on which coupling section 4 is provided.

Section 15.1 is roughened on the outer face by suitable structuring or by particles, for example diamond particles, which are applied on the surface of section 15.1 and produce a suitable roughness.

When the handpiece is switched on, the oscillating motion of handpiece coupling 2 causes the respective tool 5, 8, 10, 12, 14 connected to handpiece 1 also to move in an oscillating manner, and more precisely in an axial direction which essentially corresponds to the longitudinal elongation of the respective tool. Especially when use is made of somewhat more three-dimensional tools 12 and 14, the drive of handpiece coupling 2 can also be such that this coupling and, therefore, the tool 12 or 14 connected to the handpiece performs, in addition to the oscillating motion in the coupling axis or instead of this oscillating motion, a back and forth motion, i.e. an oscillating swivelling or rotating motion about the coupling axis, for example through an angular range of less than 90°. Whereas the tools represented in FIGS. 2-7 are used for preparing tissue, in particular in bone tissue, there are reproduced in FIGS. 8-10 various tools of the system according to the invention which are used for careful displacement of tissue or soft tissue, in particular also for use in the upper jaw region for careful displacement or removal of so-called Schmidt's membrane.

Figure 8:
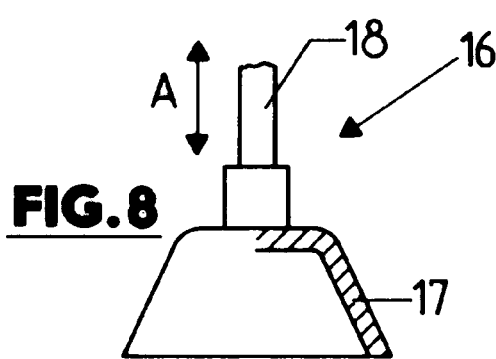
FIG. 8 is an alternate embodiment of a side view of a dental tool with the section that attaches to the coupling not shown.

Tool 16 represented in FIG. 8 essentially comprises a bell-shaped tool body or head made of an elastic or rubber-elastic material and a rigid ram 18, which is connected at one end to the middle of tool body 17 and at its other end (not represented) comprises coupling section 4. By placing tool 16, or more precisely tool body 17, on an opening formed or present in the tissue, the soft tissue surrounding this opening can be carefully displaced by the oscillating motion of tool body 17 and by the pumping motion thereby generated by tool body 17. Tool body 17 can be shaped in different ways on its open side lying opposite ram 18, for example with a round, oval or polygonal cross-section, for example a square or rectangular cross-section etc.

Figure 9:
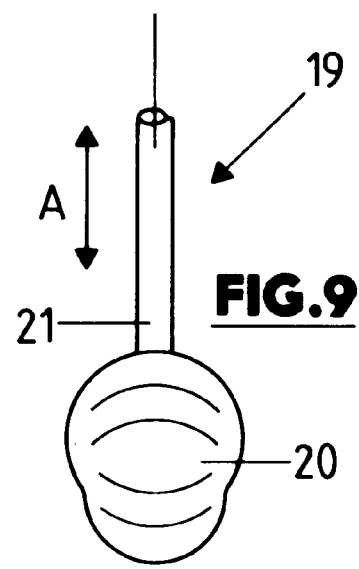
FIG. 9 is an alternate embodiment of a side view of a dental tool with the section that attaches to the coupling not shown.

FIG. 9 shows a tool 19, which essentially comprises an elastic tool body 20 and a rigid ram 21, to one end whereof tool body 20 is fixed and the other end whereof can be coupled to hand-held device 1 via coupling section 4 (not represented), and more precisely for an axial oscillating motion of ram 21 corresponding to double arrow A. Elastic tool body or head 20 is correspondingly deformed by the oscillating motion of the ram, so that an all-round displacement of the tissue is achieved after the introduction of this tool body into a tissue recess and in the presence of ram 21 driven in an oscillating manner. Tool body 20 is produced for example completely from a rubber-elastic material or comprises a tightly sealed deformable outer envelope, which is filled with a suitable material, for example with a gel or a liquid.

Figure 10:
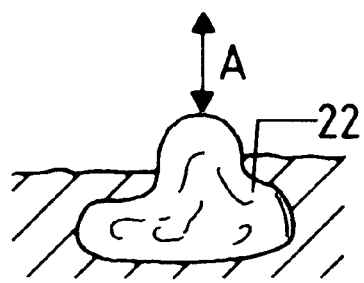
FIG. 10 is a side view of a deformable cushion that is used with a dental tool embodying the invention.

FIG. 10 shows an elastically deformable cushion 22 in the form of a gel cushion, which together with tool 16 is suitable for a careful displacement of tissue, in particular also for careful removal of Schmidt's membrane. Cushion 22 is inserted for this purpose into a suitable tissue opening and is then acted upon, on its region projecting out of this opening, by tool 16 with the oscillating motion of hand-held device 1. Cushion 22 thus forms, together with tool 16, a two-part tool, the tool head whereof is essentially a cushion 22.

Tools 5, 8, 11, 12 and 14, or more precisely their tool bodies 6, 9, 11, 13 and 15, are each made of steel, preferably of highly elastic steel with a high load-bearing capacity. In principle, the tools of the oscillating system according to the invention for preparing and displacing tissue are designed as tools for one-time use, which are disposed of on each occasion after the completion of an operative intervention on a patient.

Figure 11:
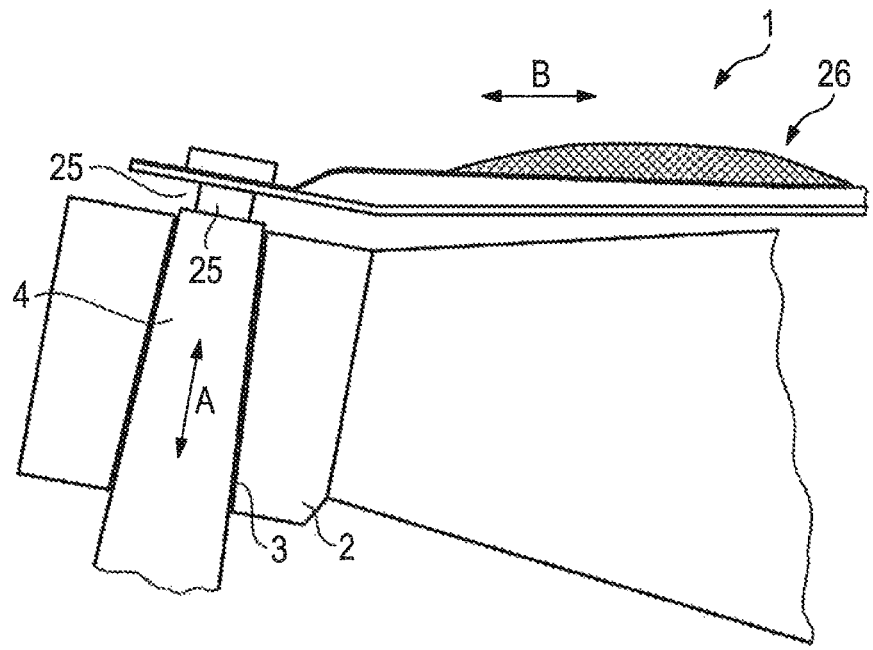
FIG. 11 is a side view of a dental handpiece with a handpiece coupling and a securing element for a dental tool shown in cutaway.
Figure 12:
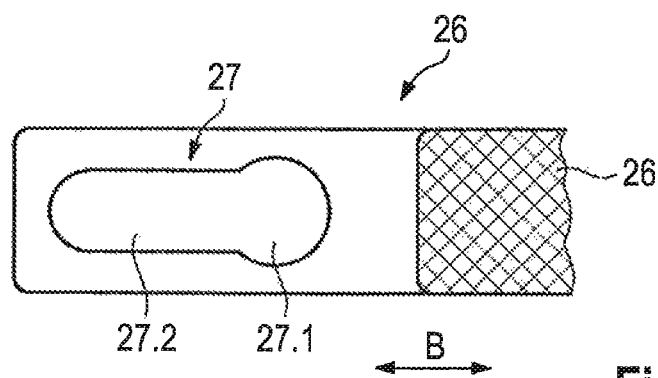
FIG. 12 is a top view of the securing element of FIG. 11.

FIG. 11 shows, again in a partial representation, a medical handpiece 1 with handpiece coupling 2, which can be driven in an oscillating manner in the direction of double arrow A by means of a drive (not represented), and a coupling section 4 of a tool or an instrument insert, otherwise not represented further, said coupling section being fixed in said coupling. In order to secure coupling section 4 in coupling opening 3, which again tapers conically towards the upper end of coupling 2, coupling section 4 projects out of the upper end of coupling opening 3 having the smaller diameter and is provided at its projecting end with an annular groove 25, which cooperates with a manually operable securing element 26 provided on medical handpiece 1 or on coupling 2. In the embodiment represented, securing element 26 is formed by a slide bar, which can be displaced radially or approximately radially with respect to the peg-like coupling section and which, in a state securing coupling section 4 to handpiece 1, engages in a form-fit manner behind this coupling section at annular groove 25 and rests on the upper side of coupling 2 and, in a non-securing position, is disengaged from annular groove 25. In the embodiment represented, the slide bar forming securing element 26 comprises for this purpose a keyhole-like opening 27, and more precisely with an opening section 27.1 with a larger cross-section, which is at least equal to the cross-section of the end of coupling section 4 projecting from coupling opening 3, and with an opening section 27.2, the width whereof is equal or roughly equal to the diameter that coupling section 4 has in the region of the annular groove.

Securing element 26 is guided in a sliding manner at the upper side of coupling 2, and preferably in such a way that, after the introduction of coupling section 4 into opening section 27.2, an axial bracing of coupling section 4 in conical coupling opening 3 takes place. Securing element 26 is provided at the upper side with a gripping area 28 for the manual operation. By means not represented, coupling section 4 is held in a torsion-proof manner in coupling opening 3 after the securing with securing element 26. This is achieved by the fact that the cross-section of coupling opening 3 and of coupling section 4 are not constituted rotationally symmetrical to the axis of coupling opening 3 and coupling section 4 and/or are profiled in a suitable way.

Figure 13:
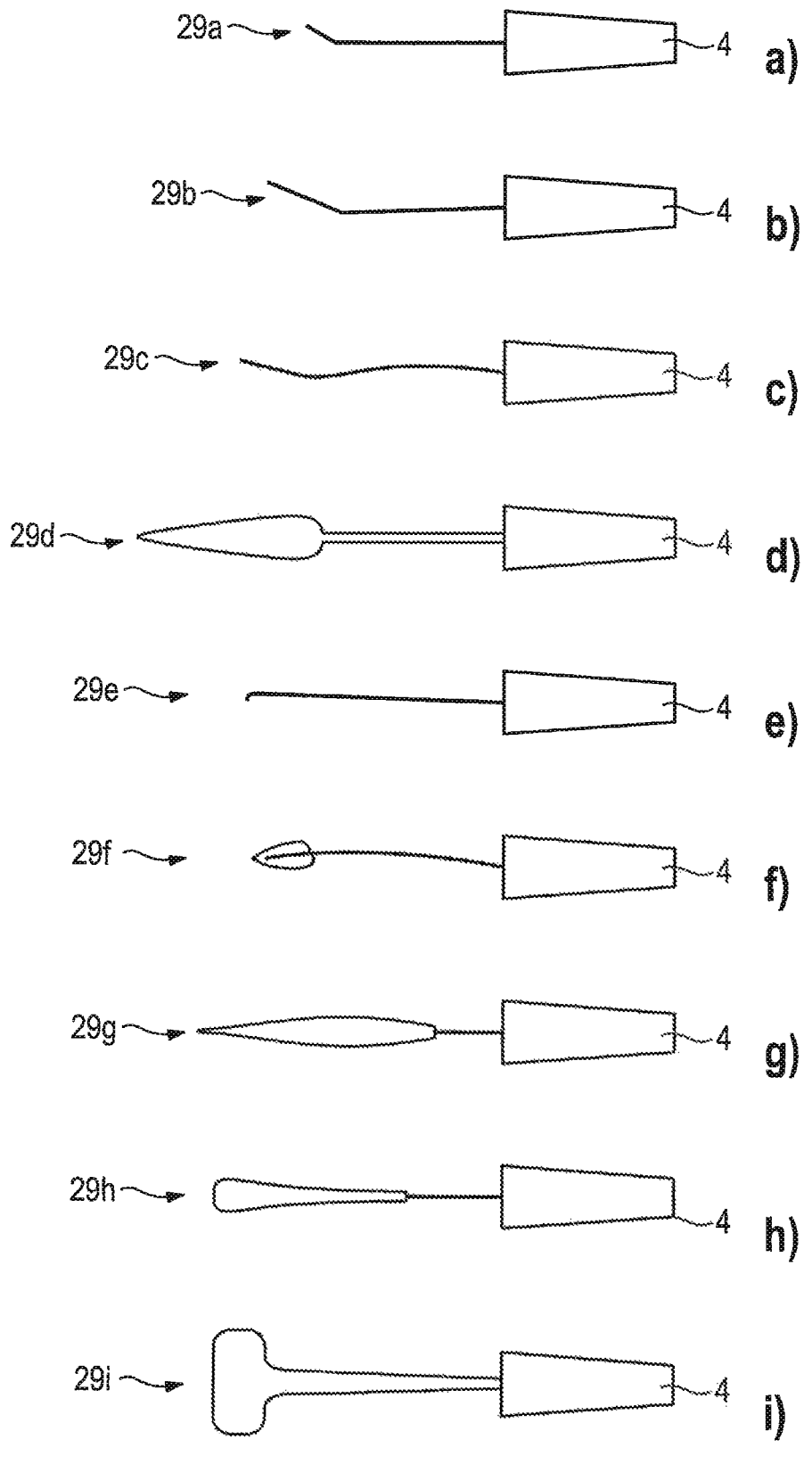
FIGS. 13a-13i show alternate embodiments of dental tools with coupling section and instrument inserts for attachment to the dental handpiece not shown.

FIG. 13 shows, in positions a-i, various tools or instrument inserts 29a-29i, which in each case comprise the actual tool body and coupling section 4 or a handgrip and which are designed as blades or cutting or splitting tools and are intended primarily for tissue surgery.

Instrument inserts 29a-29i, which are represented in FIG. 13 and which are constituted as cutting tools, can be described in greater detail in that the instrument inserts or tools each comprise a tool body projecting from coupling section 4, said tool body being formed flat at least at its free end and being constituted therewith a blade on at least one longitudinal side and/or also on the free end. The tool bodies are produced from a metallic flat material suitable for sliding tools.

The free ends of the tool bodies are slightly bent off in the case of instrument inserts 29a-29c, wherein the length of the bent-off portion varies and, in the case of instrument insert 29c, the tool body is slightly arched on its partial length following coupling section 4. In the case of instrument insert 29e, the tool body is constituted essentially rectilinear. In the case of tools 29d, 29f and 29g, the tool body is in each case constituted, proceeding from coupling section 4, with a partial length with a reduced width and, following the latter, with a partial length with an increased width, the latter forming the free end of the tool body and tapering in turn towards this free end, for example flame-like. Tool inserts 29h and 29i possess a tool body which has a reduced width on its partial length following coupling section 4 and is constituted with an increased width at the free end, wherein the width in the case of tool 29h increases continuously over a relatively great length and, in the case of instrument insert 29i, increases in a more abrupt manner in the region of the free end of the tool body. In the case of instrument inserts 29h and 29i, the blade is in each case constituted essentially also at the rounded free end of the tool body.

Figure 14:
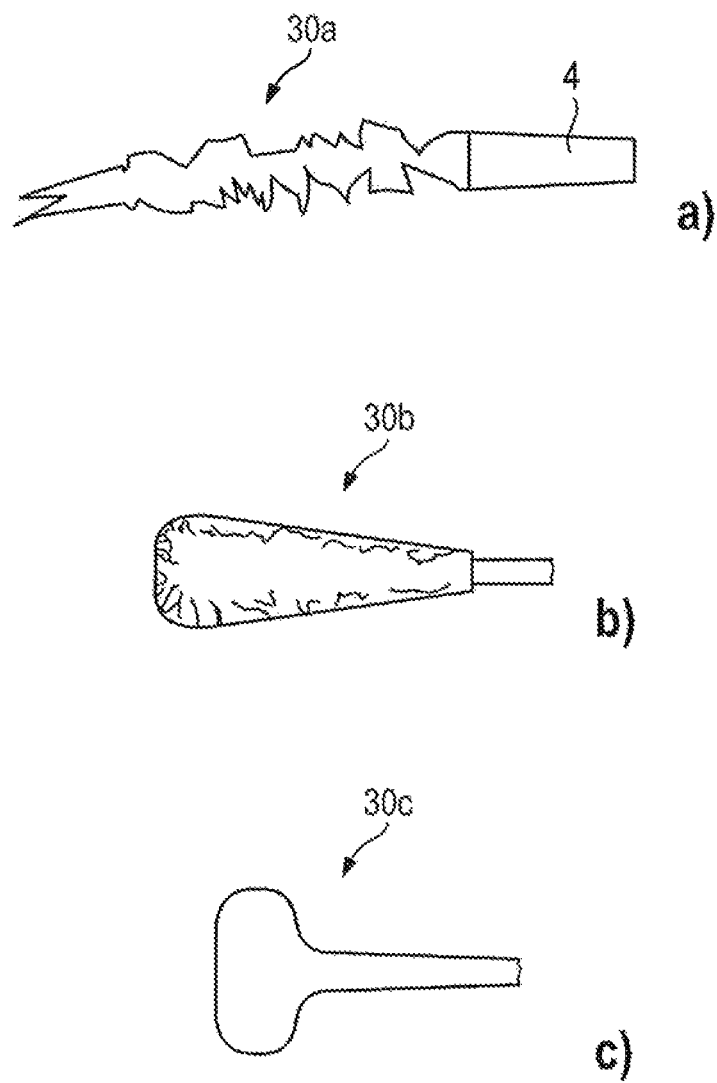
FIGS. 14a-14c show alternate embodiments of dental tools and tool ends.

FIG. 14 shows, in a simplified representation and in positions a-c, further tools or instrument inserts, which are also intended primarily for bone surgery just like the tools of FIGS. 2-7; tool 30a represented in FIG. 14 is constituted as a bone saw, and more precisely with a flat tool body, which is provided with a sawtooth-like structure on its upper and lower longitudinal side in position a. A distinctive feature consists in the fact that tool 30a is constituted with a double tip at its free end.

Tools 30b and 30c are also constituted as bone saws, and more precisely such that the flat tool body widens towards the free end. In the case of tool 30b, the longitudinal sides and also the free end are each provided with a sawtooth-like profiling. In the case of tool 30c, the sawtooth-like profiling is provided essentially at the edge of the widened region forming the free end of the tool and on the end face of this region.

Tools or instrument inserts 30a-30c are again constituted flat, but can, in addition to the sawtooth-like profiling at the longitudinal sides, also be provided on their surface sides with material-elevating profiling or a coating, for example with a diamond coating.

Figure 15:
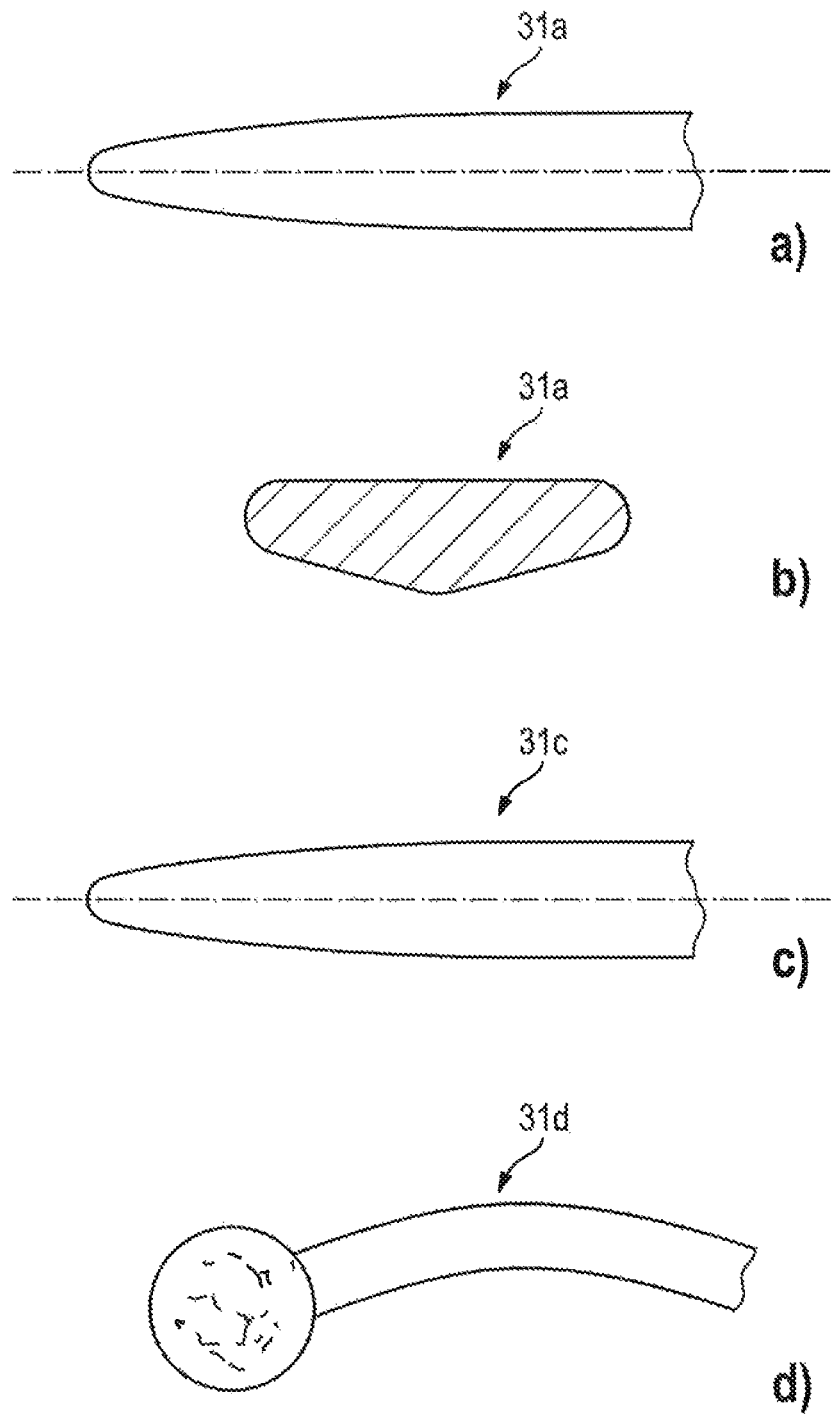
FIGS. 15a-15d show alternate embodiments of dental tools and tool ends.

FIG. 15 shows in positions a-d various tools 31a, 31c and 31d, and once again tools primarily for bone surgery, although as grinding and smoothing tools. Tool 31a is reproduced in position a in a partial representation and in a side view and in position b in cross-section. As position b shows, tool 31a has an oval cross-section, such that, of the two longer cross-sectional sides lying opposite one another, the upper cross-sectional side in position b is markedly more rectilinear than the lower cross-sectional side in this position, which is arched in a more convex shape about an axis parallel to the longitudinal axis of the tool. The shorter cross-sectional sides form rounded-off corners.

Tool 31c reproduced in side view in position c is also a tool body tapering towards the free end of this tool and rounded off there, but with a circular or essentially circular cross-section.

Tool 31d represented in position d essentially corresponds in terms of its shape to the tool with a spherical tool end represented in FIG. 4.

Instrument inserts 31a, 31c and 31d are provided on the faces of their tool body with profiling, surface structuring and/or a coating which makes these tool inserts suitable as grinding and/or smoothing tools. The surface coating is for example a diamond coating; instrument inserts 31a, 31c and 31d are preferably each present in a set, and more precisely with identical instrument inserts in each set, but with profiling or a surface coating of differing roughness, for example with a diamond coating of differing grain size. In principle, there is also the possibility of providing instrument inserts 31a, 31c and 31d in different surface regions with different profiling or roughness and/or surface structuring with diamond coatings of differing grain size.

Figure 16:
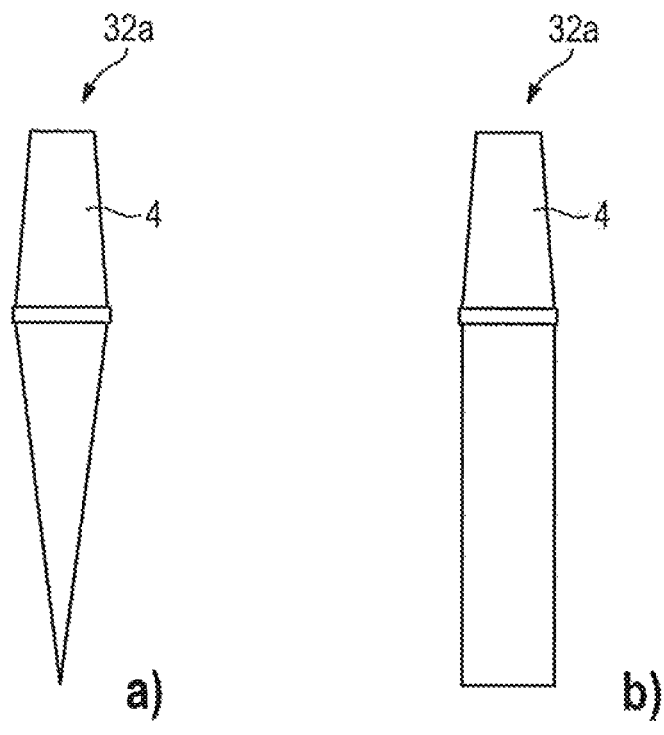
FIGS. 16a-16c show alternate embodiments of dental tools and tool ends.
Figure 16:
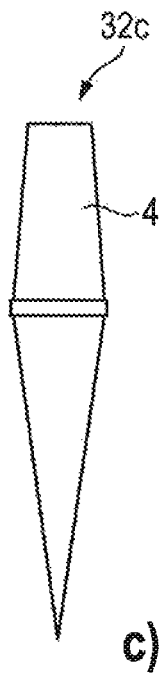

FIG. 16 shows in positions a-c further tools or instrument inserts 32a and 32c primarily for bone surgery, and more precisely in positions a and b, in two side views rotated through 90°, an instrument insert 32a constituted as a splitter with a wedge-like tool body forming at the free end an essentially rectilinear blade and coupling section 4 at the other end and, in position c, an instrument insert 32c constituted as a tip with a conical tool body and coupling section 4.

Figure 17:
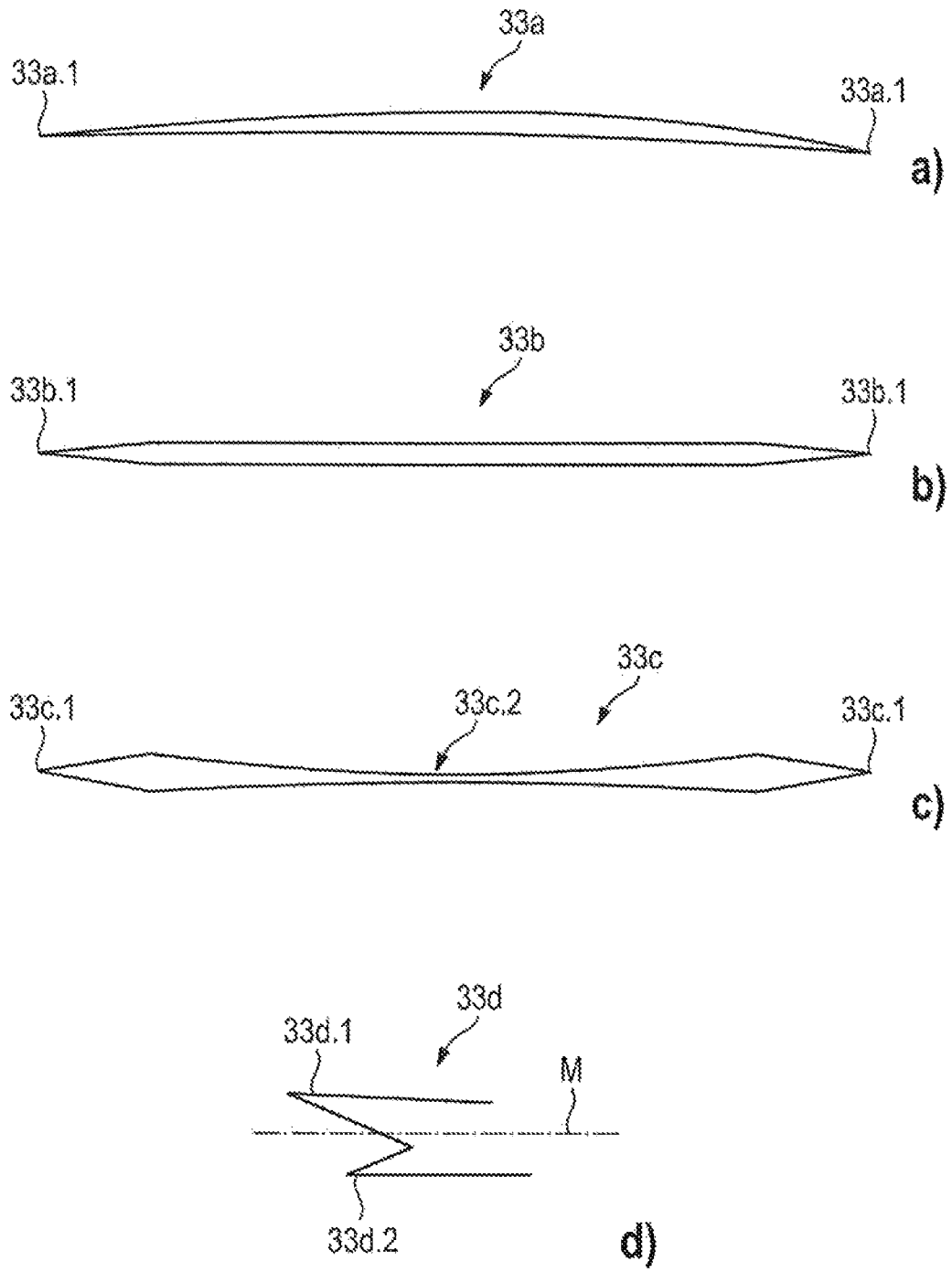
FIGS. 17a-17d show alternative embodiments of dental tools.

FIG. 17 shows in positions a-d various cross-sections through the tool body of innovative instrument inserts, in particular for tissue and bone surgery with an essentially flat formation of the tool bodies. In the case of instrument insert 33a represented in position a, the tool body is constituted such that over its whole width it has a slight curvature normal to the longitudinal extension, but at least on one surface side, i.e. in the representation of the figure on the upper surface side, is curved in a slightly convex manner in order to form blades 33a.1 on the two longitudinal sides, whereas the lower surface side is essentially rectilinear or only slightly arched in a concave manner, especially in the region of the longitudinal sides, or more precisely blades 33a.1.

In the case of instrument insert 33b of position b, the again flat tool body is shaped for the formation of the two blades 33b.1 on the longitudinal sides of the tool body in such a way that the upper and lower side of the tool body run together with a continuous reduction of the tool body thickness in each case towards blade 33b.1.

The tool body of the tool body represented in position c corresponds for example to the tool body of instrument inserts 33a or 33b, but is tapered waist-like in the middle between blades 33c.1, i.e. the tool body has a reduced thickness or waste-like section 33c.2 in the middle region, for example over its whole length.

When the tool insert is designed for bone surgery, the cutting edges are constituted on the longitudinal sides of the flat tool body in the manner as represented, for example, for the instrument insert 33d in position d, and more precisely for example saw-like with teeth 33d.1 and 33d.2 forming cutting edges, said teeth being provided for example on both sides of central plane M of the flat tool body, and for example also in a form such that the teeth or cutting edges alternate on the one and other side of central plane M in the longitudinal direction of the cutting edge, or the cutting edges or the cutting teeth forming these edges are provided in each case in pairs along the cutting edge, wherein for example each pair then comprises in each case a tooth 33d.1 of greater height and a tooth 33d.2 of smaller high and the arrangement of the teeth in the pairs in relation to central plane M is different in the longitudinal direction of the tool body or the longitudinal direction of the cutting edge.

In principle, there is also the possibility of constituting the insert intended for bone surgery, on at least one longitudinal side of the tool body, with two continuous blades each extending over the whole cutting edge or the whole tool body and arranged on both sides of central plane M.

Figure 18:
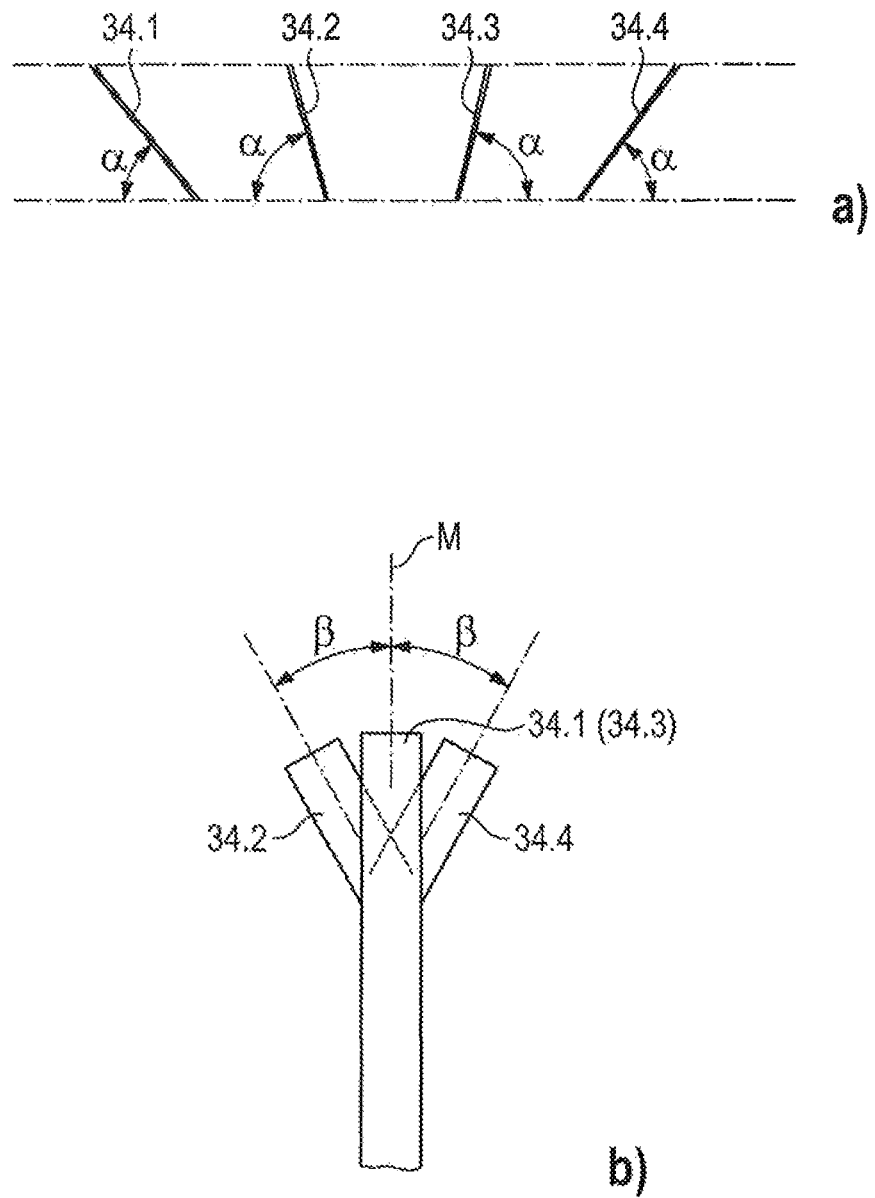
FIGS. 18a and 18b display cutting edges for attachment to a dental tool embodying the invention.

FIG. 18 shows very schematically in positions a and b the arrangement or orientation of the cutting edges in the case of an instrument insert constituted as a bone saw, wherein the course of cutting edges 34.1-34.4 formed by sawtooth-like profiling along a partial length of the instrument insert is represented schematically and in a projection onto the surface sides of the essentially flat tool body in position a. As can be seen in position a, the orientation or angle α, which is enclosed by cutting edges 34.1-34.4 formed by the sawtooth-like profiling with the longitudinal extension of the tool body, changes in the longitudinal direction of the tool body, and more precisely, in the embodiment represented, such that angle α of cutting edges 34.1 and 34.2 opens to the left at one end of the tool body, i.e. in the selected representation, but is greater in the case of cutting edge 34.2 than in the case of cutting edge 34.1, and in the case of cutting edges 34.3 and 34.4 opens to the right at the other end of the tool body, i.e. in the representation, wherein angle α is greater in the case of cutting edge 34.3 than in the case of cutting edge 34.4.

Cutting edges 34.1-34.4 follow one another in the sequence of their numbering in the longitudinal direction of the tool body. In position b, the orientation of cutting edges 34.1-34.4 is also represented schematically in a cross-section normal to the longitudinal extension of the tool body. As can be seen from position b, cutting edges 34.1 and 34.3 lie in central plane M of the flat tool body in the embodiment represented, whereas cutting edges 34.2 and 34.4 form with central plane M an acute angle β, which opens towards the edge of the tool body, and in such a way that cutting edges 34.2 and 34.4 project over different sides of central plane M.

The tool body is constituted such that a plurality of sequences comprising cutting edges 34.1-34.4 adjoins one another and/or follows one another in the longitudinal direction of the tool body. Here, however, it is in particular possible for the number of cutting edges in the individual cutting-edge sequences to be larger or smaller than previously and/or for each cutting-edge sequence to be constituted for example such that the respective last cutting edge of a cutting-edge sequence forms the first cutting edge of a following identical cutting-edge sequence. In the example represented in FIG. 18, this means that the cutting-edge sequence comprises not only cutting edges 34.1-34.4, but following on from cutting edge 34.4 again cutting edge 34.3, cutting edge 34.2 following the latter and cutting edge 34.1 following thereon.

The invention has been described above using examples of embodiment. It goes without saying that numerous changes and modifications are possible without thereby departing from the inventive idea underlying the invention.

LIST OF REFERENCE NUMBERS

1 dental handpiece
2 handpiece coupling
3 coupling opening
4 coupling section on tool
5 tool
6 tool body
7 recess
8 tool
9 tool body
10 tool
11 tool body
11.1, 11.2 section of tool body 11
12 tool
13 tool body
14 tool
15 tool body
15.1, 15.2 section of tool body 15
16 tool
17 bell-shaped elastic tool body
18 rigid ram
19 tool
20 rigid ram
21 elastic tool body
22 elastic cushion
25 annular groove
26 securing element or securing slide bar
27 opening in securing element 26
27.1, 27.2 opening section
28 gripping area
29-33 tool
A oscillating motion
B movement direction of securing element
M central plane
KA axis of coupling 2

The invention claimed is:

1. A dental system for preparing and displacing tissue, comprising:
    a dental handpiece comprising a drive;
    a handpiece coupling; and
    a tool shaped and dimensioned for selective insertion in the dental handpiece coupling, wherein the dental handpiece coupling and the tool are driven by the drive in an oscillating manner and wherein the tool comprises a cutting tool, the cutting tool is a bone saw having cutting edges of cutting blades arranged on opposite sides of a central plane M, such that when viewed from a position a, an angle α, from a longitudinal axis, spaces each of the cutting blades on either side of the central plane M, such that the angle α for cutting edges opens to the left in a first direction at one end of a tool body and opens to the right in a second direction at another end of the tool body, wherein the angle α is greater in the case of a first inner cutting edge than in the case of a second outer cutting edge on either end of the tool body taken from a center line, and wherein when viewed from a position b, the cutting edges of the cutting blades on opposite sides of the central plane M form with the central plane M an acute angle β, acute angle β opens towards an edge of the tool body in such a way that the cutting edges are on opposite sides of the central plane M and project over different sides of the central plane M and wherein the cutting edges of the cutting blades follow one another in a sequence in a longitudinal direction of the tool body.

2. The system according to claim 1, wherein the system further includes a tool having a surface roughness on at least a partial region of a surface of a body of the tool.

3. The system according to claim 1, wherein the system further includes a tool comprising an elastic tool head which is connected to the handpiece coupling by means of a rigid or essentially rigid tool section.

4. The system according to claim 3, wherein the elastic tool head is bell-shaped.

5. The system according to claim 3, wherein the elastic tool head is a body comprising a tightly sealed deformable outer envelope filled with a liquid or a gel.

6. The system according to claim 5, wherein the elastic tool head is formed by an elastic cushion.

7. The system according to claim 1, wherein the handpiece coupling is driven by the drive for an oscillating motion in an axial direction of the coupling or for an oscillating swivelling motion about the axis of the coupling.

8. The system according to claim 1, further comprising a manually operable securing element on the handpiece for securing the tool.

9. The system according to claim 1, wherein the system further includes a tool having a tool body curved at least on a partial region about at least one axis extending in the longitudinal direction of the tool body, or has a reduced thickness or is tapered with a reduced thickness in the longitudinal direction of the tool body.

\* \* \* \* \*